US012635942B2

(12) United States Patent
Lau

(10) Patent No.: US 12,635,942 B2
(45) Date of Patent: May 26, 2026

(54) HAND TEMPERATURE MONITORING DEVICE FOR CHINESE MEDICINE DIAGNOSIS AND TREATMENT

(71) Applicant: AP Infosense Limited, Hong Kong (HK)

(72) Inventor: Kam Chiu Lau, Rockville, MD (US)

(73) Assignee: AP Infosense Limited, Hong Kong (HK)

( * ) Notice: Subject to any disclaimer, the term of this patent is extended or adjusted under 35 U.S.C. 154(b) by 510 days.

(21) Appl. No.: 18/261,278

(22) PCT Filed: Aug. 1, 2022

(86) PCT No.: PCT/IB2022/057107
§ 371 (c)(1),
(2) Date: Jul. 13, 2023

(87) PCT Pub. No.: WO2023/026116
PCT Pub. Date: Mar. 2, 2023

(65) Prior Publication Data
US 2024/0065624 A1 Feb. 29, 2024

(30) Foreign Application Priority Data
Aug. 26, 2021 (CN) .......................... 202122035194.7

(51) Int. Cl.
*A61B 5/00* (2006.01)
*A61B 5/01* (2006.01)

(52) U.S. Cl.
CPC ............ *A61B 5/4854* (2013.01); *A61B 5/015* (2013.01); *A61B 5/6825* (2013.01); (Continued)

(58) Field of Classification Search
CPC .............. A61B 5/015; A61B 2562/046; A61B 2562/12; A61B 5/4854; A61B 5/6825; (Continued)

(56) References Cited

U.S. PATENT DOCUMENTS

| | | | | |
|---|---|---|---|---|
| 6,180,867 B1 * | 1/2001 | Hedengren | .............. | G01K 7/02 374/E7.004 |
| 11,868,178 B2 * | 1/2024 | von Badinski | ........ | G04G 21/02 |

(Continued)

FOREIGN PATENT DOCUMENTS

| | | |
|---|---|---|
| CN | 105136326 A | 12/2015 |
| CN | 108471946 A | 8/2018 |

(Continued)

OTHER PUBLICATIONS

Translation of CN-109506804-A (Year: 2019).*

*Primary Examiner* — Jon Eric C Morales
(74) *Attorney, Agent, or Firm* — Idea Intellectual Limited; Sam T. Yip

(57) ABSTRACT

A hand temperature monitoring device includes at least one sensing array composed of a flexible printed circuit board (110), temperature sensors (120), p-type metal oxide semiconductor field-effect transistors (MOSFETs) (130), polymer films (140) and carbon fiber boards (150). The temperature sensors (120) are disposed on a first side (112) of the flexible printed circuit board (110). The p-type MOSFETs (130) are disposed on a second side (114) of the flexible printed circuit board (110) opposing to the temperature sensors (120), wherein each of the p-type MOSFETs (130) is electrically connected to one of the temperature sensors (120). The polymer film (140) encapsulates each of the temperature sensors (120) and the p-type MOSFETs (Continued)

100

(130) respectively. The carbon fiber board (150) is positioned over the polymer film and spaced apart from the polymer film (140).

28 Claims, 6 Drawing Sheets

(52) U.S. Cl.
CPC ...... *A61B 5/7225* (2013.01); *A61B 2562/046* (2013.01); *A61B 2562/12* (2013.01)

(58) Field of Classification Search
CPC ... A61B 5/7225; A61B 5/743; A61B 10/0012; A61B 2010/0019; A61B 2560/0214; A61B 2560/0412; A61B 2562/146; A61B 2562/164; A61B 2562/166; A61B 5/01; A61B 5/0205; A61B 5/021; A61B 5/02416; A61B 5/1118; A61B 5/14532; A61B 5/1455; A61B 5/332; A61B 5/349; A61B 5/681; A61B 5/6826; G01K 13/20; G01K 1/143; G01K 3/14; G01K 7/02; G01K 7/22; A61F 2/5046; A61F 2/583; A61F 2/586; A61F 2/72; A61F 2002/501; A61F 2002/5053; A61F 2002/5055; A61F 2002/5061; A61F 2002/5066; A61F 2002/5089; A61F 2002/587; A61F 2002/6827; A61F 2002/6863; A61F 2002/701; A61F 2002/704; A61F 2002/7635

See application file for complete search history.

(56) References Cited

U.S. PATENT DOCUMENTS

| | | | |
|---|---|---|---|
| 2012/0263209 A1 | 10/2012 | Panda et al. | |
| 2021/0085491 A1* | 3/2021 | Akhtar | A61F 2/583 |

FOREIGN PATENT DOCUMENTS

| | | | | |
|---|---|---|---|---|
| CN | 109506804 A | * | 3/2019 | A61B 10/0012 |
| CN | 109974877 A | | 7/2019 | |
| CN | 216386041 U | | 4/2022 | |

* cited by examiner

100

HAND TEMPERATURE MONITORING DEVICE FOR CHINESE MEDICINE DIAGNOSIS AND TREATMENT

CROSS REFERENCE OF RELATED APPLICATION

This application claims priority from Chinese utility model patent application number No. 202122035194.7 filed on Aug. 26, 2021, which is hereby incorporated herein by reference in its entirety for all purposes.

FIELD OF THE INVENTION

The invention relates to the technical field of temperature monitoring device. In particular, it relates to a hand temperature monitoring device for Chinese medicine diagnosis and treatment.

BACKGROUND OF THE INVENTION

Changes in the temperature of the hands can help Chinese medicine diagnosis. If the center of the palm is too warm, it is usually an early sign of biliary and an upset digestion system. If the back of the hand is warmer than the palm, there may be a fever or acute inflammation. If the palm has a higher temperature at the outskirt and a lower temperature in the center, it may indicate high concentration of blood lipids or high blood pressure. If the palm becomes too warm and dry, there may be a problem with the thyroid glands. It is often found that a person who has cold hands usually has poor general health. In some cases, cold hands or cold fingers may indicate poor blood circulation. A person with high fever and cold hands is likely to faint or, in a more severe case, fall into a convulsive coma. Cold palms indicate weak digestion and absorption in the spleen and stomach.

The changes of temperatures at different positions on the hands correspond to different health issues. In the clinical diagnosis and treatment of traditional Chinese medicine, the temperature change in different areas of a person's hands can be used as a diagnostic index to the underlying health issues. For example, there is a correlation between hyperthermia, especially a feverish sensation at chest, palms, and soles, and the degree of temperature in the palms. An increase of the palm temperature is an important indicator of whether a person is suffering from hyperthermia. This diagnostic index is particularly pronounced in a person who has been diagnosed with yin-deficiency.

It is important to have accurate readouts of the temperature at different areas of a hand in real time because the change of temperature also provides information about a person's health. Conventional hand temperature monitoring devices cannot capture the temperature of an entire hand in real time. The finger tips have smaller surface area, and their temperatures are difficult to capture. The lack of sensitivity in the conventional hand temperature monitoring devices is a problem that needs to be addressed because the lack of sensitivity can be translated as lack of accuracy in diagnosis. Furthermore, a hand temperature monitoring device has to endure thousands of contacts in its service life. The sensing units in the device are prone to wears and damage due to the frequent contacts. A more durable design that will protect the sensing units is also in urgent need.

SUMMARY OF THE INVENTION

This section is for the purpose of summarizing some aspects of embodiments of the invention and to briefly introduce some further embodiments. In this section, as well as in the abstract and the title of the invention of this application, simplifications or omissions may be made to avoid obscuring the purpose of the section, the abstract and the title, and such simplifications or omissions are not intended to limit the scope of the invention.

The present invention has been made in view of the above-mentioned problems of a more durable hand temperature monitoring device with high accuracy.

Accordingly, one aspect of the present invention provides a hand temperature monitoring device includes at least one sensing array composed of a flexible printed circuit board, temperature sensors, p-type metal oxide semiconductor field-effect transistors (MOSFETs), polymer films and carbon fiber boards. The temperature sensors are disposed on a first side of the flexible printed circuit board. The p-type MOSFETs are disposed on a second side of the flexible printed circuit board opposing to the temperature sensors, wherein each of the p-type MOSFETs is electrically connected to one of the temperature sensors. The polymer films are a substantially planar layer that caps the temperature sensors 120 and the p-type MOSFETs 130 respectively. And the carbon fiber board is positioned over the polymer film.

In one embodiment of the present invention, the sensing array is flexible and bendable.

In another embodiment of the present invention, the hand temperature monitoring device may be applied to a sole based on needs.

In a further embodiment of the present invention, each of the temperature sensors is electrically independent from each other and has an individual switch.

In one embodiment, the carbon fiber board has a solid resin film layer on one side and a dry fabric layer on the opposite side. The solid resin film layer is disposed for making a full and intimate contact with a mould surface and the dry fabric layer is disposed for contacting with the polymer film for further curing.

In a further embodiment of the present invention, the hand temperature monitoring device further includes a processor having a control unit, decoders, multiplexers and a computing device. The decoders are connected between the control unit and rows of the temperature sensors. The multiplexers are connected between the control unit and columns of the temperature sensors. The computing device may be a personal computer, a laptop or a tablet. In some embodiments, the processor can be connected to a display, an external storage, a wireless module or a battery instead.

In a further embodiment of the present invention, a state of an individual temperature sensor is configured to change based on a switching signal generated by the control unit.

In a further embodiment of the present invention, the carbon fiber board is secured to the polymer film which is attached to the flexible printed circuit board by temperature sensors or the p-type MOSFETs. More particularly, the carbon fiber board is laid onto the polymer film with the dry fabric layer side and put together into a vacuum bag for lamination. The dry fabric layer of the carbon fiber board 150 facilitates and completes the air removal under vacuum. After the lamination, it is fixed at a curing temperature 130-180° C.

In another embodiment of the present invention, the hand temperature monitoring device is personalized. To be more particular, a mould can be made based on subject's palm. The solid resin film layer of the carbon fiber can make a full and intimate contact with the surface of the mould to manufacture a personalized hand temperature monitoring device. Therefore, the sensing array is flexible and perfectly matched with the subject's palm.

In a further embodiment of the present invention, each of the p-type MOSFET comprises a gate electrode, a source electrode, and a drain electrode, the gate electrode is electrically connected to the flexible printed circuit board, the source electrode is electrically connected to the power source, and the drain electrode is electrically connected to the temperature sensor.

In a further embodiment of the present invention, the temperature sensors are negative temperature coefficient thermistors having two solder plated electrodes.

In a further embodiment of the present invention, the temperature sensors are doped with P-doping or Boron.

In a further embodiment of the present invention, the hand temperature monitoring device further includes a thermal cured filling disposed between the flexible printed circuit board and the temperature sensors and between the flexible printed circuit board and the p-type MOSFETs.

BRIEF DESCRIPTION OF THE DRAWINGS

In order to more clearly illustrate the technical solutions of the embodiments of the present invention, the drawings needed to be used in the description of the embodiments will be briefly introduced below. It is obvious that the drawings in the following description are only some embodiments of the present invention, and it is obvious for those skilled in the art to obtain other drawings based on these drawings without inventive exercise, in which.

Figure 1:
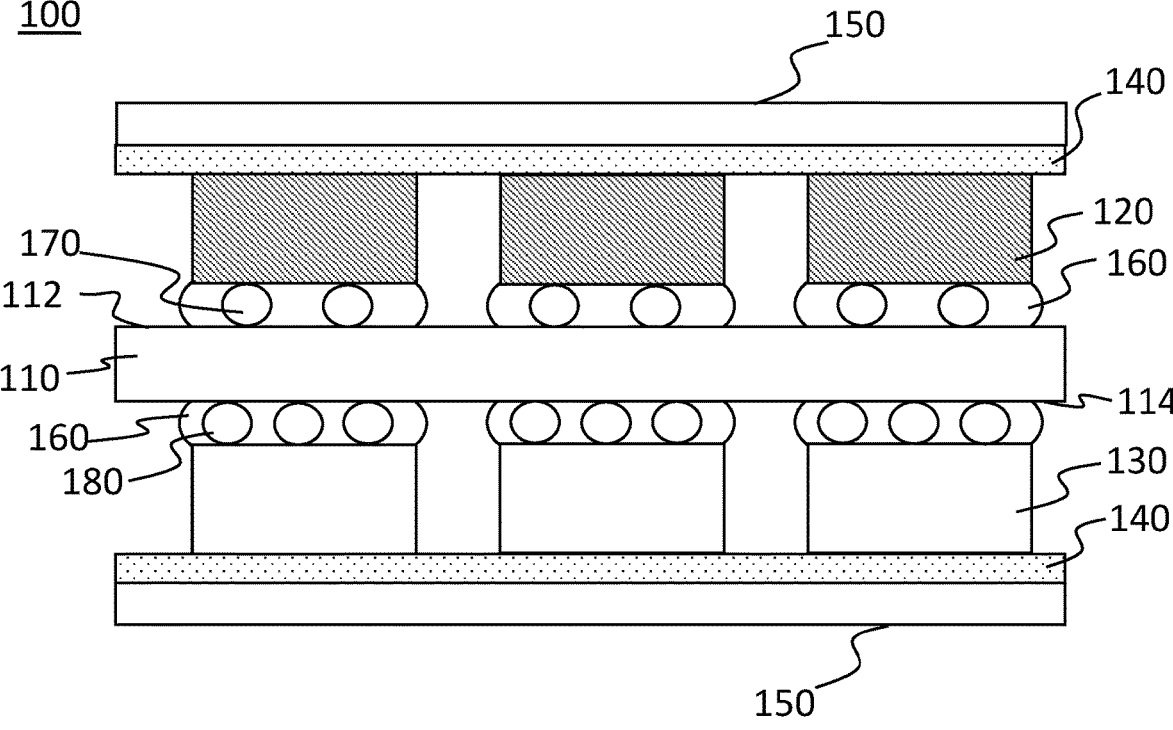
FIG. 1 is a schematic diagram showing a cross-sectional view of a sensing area of a hand temperature monitoring device according to an embodiment of the present invention

REFERENCE CHARACTERS 100 sensing array
110 flexible printed circuit board
112 first side of flexible printed circuit board
114 second side of flexible printed circuit board
120 temperature sensor
130 p-type MOSFET
140 polymer film
150 carbon fiber board
160 thermal cured epoxy
170, 180 solder joints
200 sensing circuit system
210 multiplexer
220 low noise power source
230 decoder
240 memory 250 low noise amplifier
260 processor
262 control unit
264 data transmit unit
270 computing device

DETAILED DESCRIPTION OF THE INVENTION

In order to make the aforementioned objects, features and advantages of the present invention comprehensible, embodiments accompanied with figures are described in detail below.

In the following description, numerous specific details are set forth in order to provide a thorough understanding of the present invention, but the present invention may be practiced in other ways than those specifically described and will be readily apparent to those of ordinary skill in the art without departing from the spirit of the present invention, and therefore the present invention is not limited to the specific embodiments disclosed below.

Turning to FIG. 1, a cross-sectional view of a sensing array 100 of an embodiment of the present invention is shown. The sensing array 100 includes a flexible printed circuit board 110, temperature sensors 120 and p-type metal oxides semiconductor field effect transistors (MOSFETs) 130. More particularly, the architecture of the sensing array 100 from one end to another is the carbon fiber board 150, the polymer film 140, the temperature sensors 120, the flexible printed circuit board 110, the p-type MOSFETs 130, a second polymer film 140, and a second carbon fiber board 150.

The flexible printed circuit board 110 has a first side 112 and a second side 114. The first side 112 and the second side 114 are planes opposing each other. The temperature sensors 120 are disposed on the first side 112 of the flexible printed circuit board 110 in an array. The temperature sensors 120 are arranged in parallel rows and columns. In one embodiment, the temperature sensors 120 are in a 100×100 square array on the flexible printed circuit board 110. Each of adjacent temperature sensors 120 has a center distance of 2 mm when the temperature sensors 120 are arranged in the 100×100 square array.

In one embodiment, each of the temperature sensor 120 has two electrodes, which are electrically and mechanically connected to the first side 112 of the flexible printed circuit board 110 through a pair of solder joints 170 in a welding process. The temperature sensor 120 may further include a thermal cured epoxy 160 to protect the solder joints. In one embodiment, the temperature sensors 120 are negative temperature coefficient thermistors. In one embodiment, the temperature sensors 120 are carbon fiber reinforced cement-based composite resistors. Such temperature sensors 120 can be doped with P-doping or Boron. The concentration of the dopant ranges between $5.00000e14$ $cm^{-3}$ and $6.00000e14$ $cm^{-3}$. The addition of the dopant can tune the rate of resistance that is sensitive to the temperature. In other words, though providing dopant to the temperature sensors 120, the sensitivity of the temperature sensors 120 will be increased. For example, if P-doping or Boron is added to the temperature sensors 120 in a concentration of $5.00000e14$ $cm^{-3}$, the temperature sensors 120 has high sensitivity.

The p-type MOSFETs 130 are disposed on the second side 114 of the flexible printed circuit board 110. In one embodiment, each of the p-type MOSFETs 130 has three electrodes. The three electrodes are a gate electrode, a source electrode, and a drain electrode. The p-type MOSFETs 130 are secured on the flexible printed circuit board 110 through triple solder joints 180 in a welding process. The p-type MOSFETs may further includes a thermal cured epoxy 160 to protect the solder joints 180. The p-type MOSFETs 130 are arranged in a manner that each of the p-type MOSFETs 130 corresponds to one of the temperature sensors 120 on the first side of the flexible printed circuit board 110. In other words, the p-type MOSFETs 130 on the second side 114 are in an array that mirrors the arrangement of the temperature sensors 120 on the first side 112 of the flexible printed circuit board 110.

The gate electrode of the p-type MOSFETs 130 is electrically connected to the flexible printed circuit board 110. The source electrode of the p-type MOSFETs 130 is connected to a power source. The drain electrode of the p-type MOSFETs 130 is connected to a temperature sensor 120. That is, through the drain electrode, one p-type MOSFET 130 is electrically paired with the temperature sensor 120 which is at its mirroring position on the first side 112 of the flexible printed circuit board 110.

Still referring to FIG. 1, polymer films 142 are a substantially planar layer that caps the temperature sensors 120 and the p-type MOSFETs 130 respectively. The polymer films 140 conform to the individual shape of the temperature sensors 120 and the p-type MOSFETs 130. This polymer film is electrically insulated so as to protect the temperature sensors 120 and the p-type MOSFETs 130. In one embodiment, the polymer films 140 can be discrete. In another embodiment, the polymer films 140 can join the immediately adjacent polymer films 140. This configuration of the polymer films 140 ensures the temperature sensors 120 and the p-type MOSFETs 130 being fully secured to the flexible printed circuit board 110. In one embodiment, the polymer film 140 is a polyethylene terephthalate tape and has a thickness of approximately 0.01 mm.

A carbon fiber board 150 is disposed on the polymer films 140. The carbon fiber board 150 has a solid resin film layer (not shown in figure) on one side and a dry fabric layer (not shown in figure) on the opposite side. The solid resin film layer is disposed for making a full and intimate contact with a mould surface and the dry fabric layer is disposed for contacting with the polymer film 140 for further curing.

To fix the carbon fiber board 150 onto the flexible printed circuit board 110, the carbon fiber board 150 is laid onto the flexible printed circuit board 110 with the dry fabric side and put together into a vacuum bag for laminating. At this stage, the dry fabric layer of the carbon fiber board 150 facilitates and completes the air removal under vacuum. After the lamination, it is fixed at a curing temperature 130-180° C. Further, the resin layer can make a full and intimate contact with the surface of mould to manufacture a personalized hand temperature monitoring device, since the mould may be made based on a subject's palm. The flexibility of the carbon fiber board 150 matches the flexible printed circuit board 110. When the flexible printed circuit board 110 is subject to a force and therefore bends, the carbon fiber board 150 is capable of conforming to the morphology of the flexible printed circuit board 110. The carbon fiber board 150 is electrically and thermally conductive. In one embodiment, the carbon fiber board 150 has a thermal conductivity higher than copper. In one embodiment, the carbon fiber board 150 has a thermal conductivity of approximately 700 W/mk. The electronic components are densely arranged on the flexible printed circuit board 110, and the carbon fiber board 150 which has a high heat dissipation rate acts as a passive heat dissipation tool. A thickness of the carbon fiber board 150 ranges between 0.056 mm and 0.25 mm. In one embodiment, the carbon fiber board has a thickness of approximately 0.25 mm. The carbon fiber board 150 can also block sweat and grease permeation to the electronic components disposed on the flexible printed circuit board 110. The carbon fiber board 150 greatly enhances the durability and sensitivity of the hand temperature monitoring device because of its protective functions.

Figure 2:
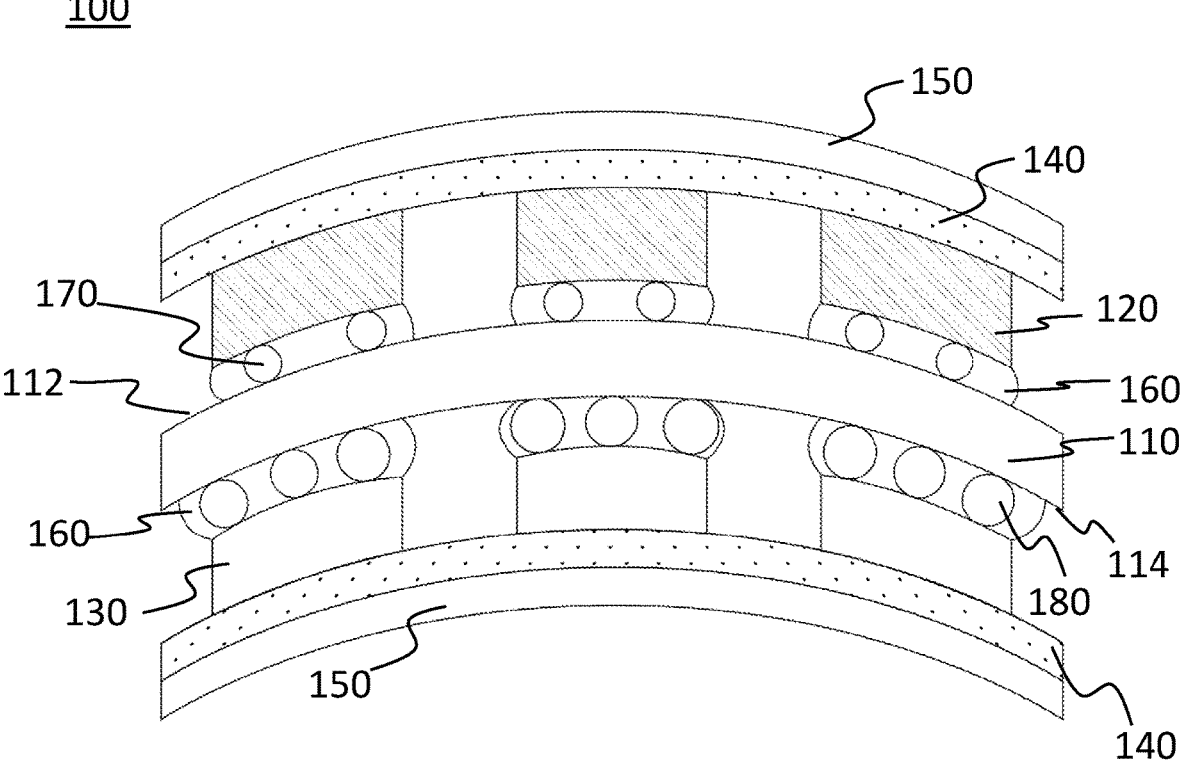
FIG. 2 is a schematic diagram showing a cross-sectional view of a sensing area of a hand temperature monitoring device according to another embodiment of the present invention.

Referring to FIG. 2, another embodiment of the present invention is depicted. The hand temperature monitoring device is personalized and the sensing array 100 can be curved. A mould (not shown in figure) can be made based on subject's palm. The solid resin film layer (not shown in figure) of the carbon fiber board 150 can make a full and intimate contact with the surface of the mould to manufacture a personalized hand temperature monitoring device. Therefore, the sensing array is perfectly matched with the subject's palm and fitted perfectly with all the curves of palm.

Figure 3:
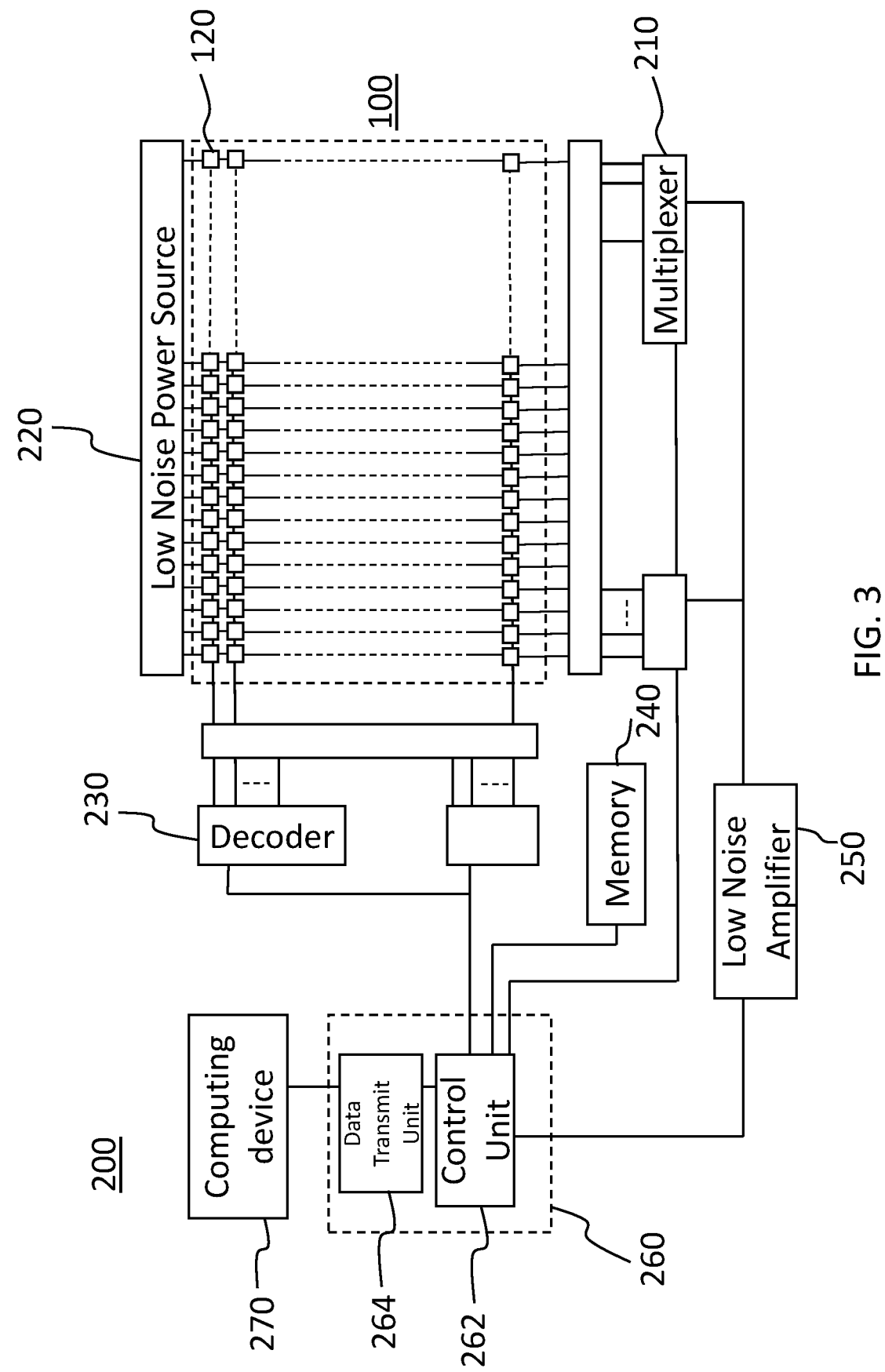
FIG. 3 illustrates an example circuit of a sensing area of a hand temperature monitoring device according to an embodiment of the present invention.

Turning to FIG. 3, a sensing circuit system 200 of the temperature monitoring device in accordance with an embodiment of the present invention is shown. The sensing circuit system 200 includes the sensing array 100, as shown in FIG. 1, multiplexers 210, a low noise power source 220, decoders 230, a memory storage 240, a low noise amplifier 250, a processor 260 having a control unit 262 and a data transmit unit 264, and a computing device. The data transmit unit 264 is a high speed required functional block for sending required control signal in a high speed to the control unit 262 and processing quantify analog signal precisely to output graphic signals to the computing device. The decoders 230 are connected between the control unit 262 and rows of the temperature sensors 120. The multiplexers 210 are connected between the control unit 262 and columns of the temperature sensors 120. The control unit 260 sends a switching signal to an individual p-type MOSFET 130, as shown in FIG. 1, for an on or off command. When a low-level signal is applied to the gate electrode of the p-type MOSFET 130, the p-type MOSFET 130 turns on. When a high-level signal is applied to the gate electrode, the p-type MOSFET 130 turns off. The p-type MOSFETs 130 act as the switch to the temperature sensors 120. More particularly, the p-type MOSFETs 130 are the switch for the individual temperature sensors 120.

As used herein, the term "computing device" refers to a hardware capable of data and/or signal calculation, transmission, processing, executing and having a display function. A computing device may be, but not limited to, a personal computer, a laptop or a tablet. Based on the needs and different using scenarios, the processor can be further connected to a display, an external storage, a wireless module or a battery.

Each p-type MOSFET 130 has three electrodes, as shown in FIG. 1, namely, the gate electrode, the source electrode, and the drain electrode. The gate electrode of the p-type MOSFET 130 is connected to a common gate bus (not shown), and the control unit 260 communicates with individual p-type MOSFET 130 through the common gate bus. The source electrode of the p-type MOSFET 130 is connected to the low noise power source 220. Each temperature sensor 120 has two electrodes. The drain electrode of the p-type MOSFET 130 is connected to one of the two electrodes of its mirroring temperature sensor 120. The one remaining electrode of the temperature sensor 120 is connected to a common bus (not shown) that joins to the multiplexer 210. By switching on and off one of the p-type MOSFET 130, the mirroring temperature sensor 120 of such p-type MOSFET 130 can be turned on or off independently from the remaining temperature sensors 120. That is, if the control unit 260 sends a low-level signal to the gate electrode of an individual p-type MOSFET 130 through the common gate bus, this one p-type MOSFET 130 is turned on, and the mirroring temperature sensor 120 is subsequently turned on. Alternatively, if the control unit 260 sends a high-level signal to the gate electrode of an individual p-type MOSFET 130 through the common gate bus, this one p-type MOSFET 130 is turned off, and the mirroring temperature sensor 120 is subsequently turned off. Therefore, the control unit 260 determines the switch on/off of temperature sensors 120 and is in charge of starting the whole detecting mechanism. This independent on/off mechanism ensures minimum electrical crosstalk among the densely packed temperature sensors 120. The readouts of the resistance are collected from individual temperature sensor 120.

Figure 4:
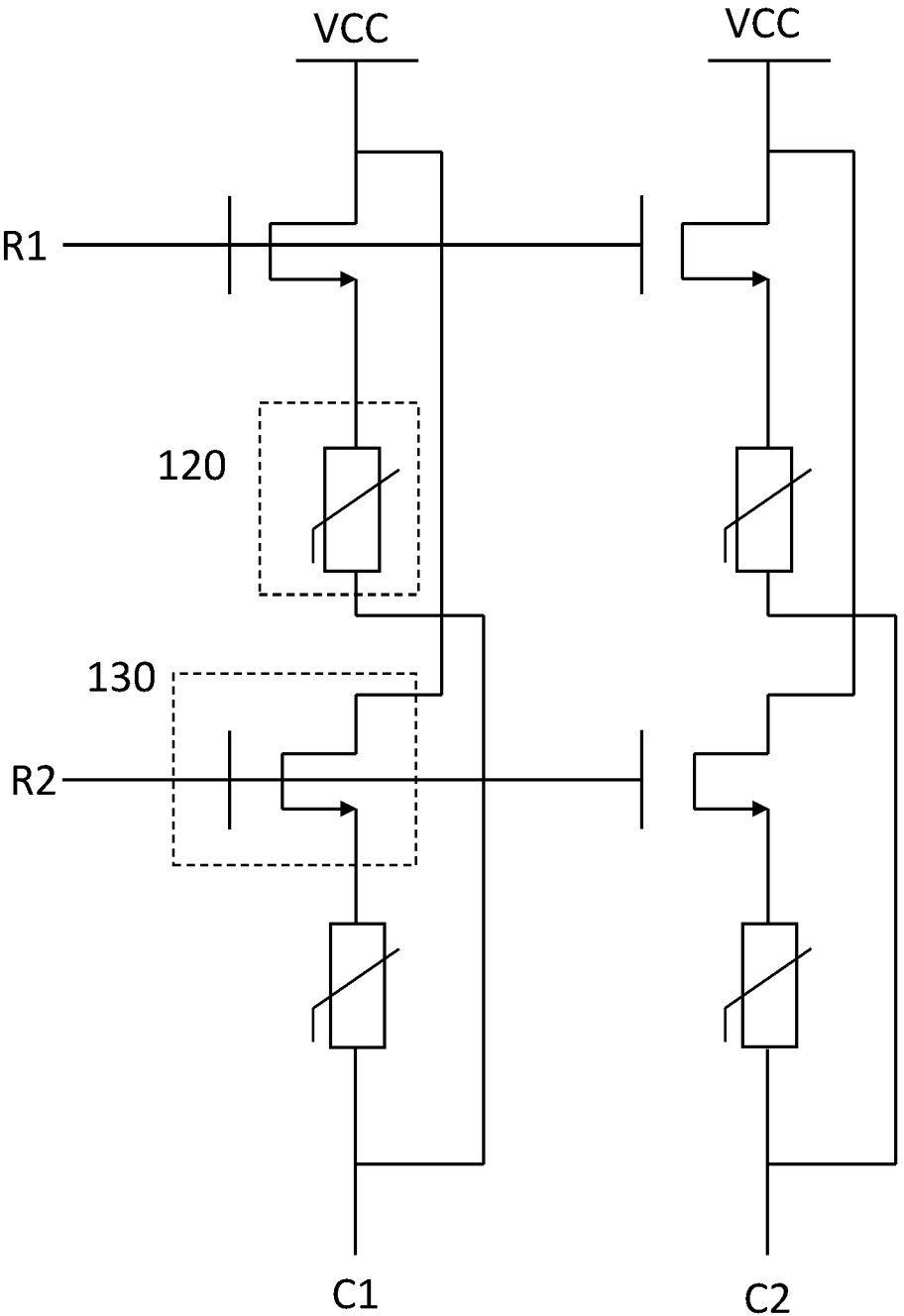
FIG. 4 is a schematic diagram showing an example circuit for monitoring hand temperature according to an embodiment of the present invention.

Turning to FIG. 4, a schematic diagram shows a portion of the circuit layout of the sensing array 100. R1 and R2 represents row 1 and row 2. C1 and C2 represents column 1 and column 2. At the coordinate (R1, C1), an individual temperature sensor 120 is placed and connected to its mirroring p-type MOSFET 130 through the drain electrode. Similarly, at the coordinate (R2, C1), another individual temperature sensor is placed and connected to its mirroring p-type MOSFET. The individual temperature sensors are electrically independent. That is, when a low-level signal is delivered from the control unit and applied to the gate electrode of the p-type MOSFET 130, the p-type MOSFET 130 turns on, and its mirroring temperature sensor 120 at the (R1, C1) receives the 'on' signal and turns on accordingly. The temperature sensor at (R2, C1) is not activated in the process. An independent 'on' or 'off' signal will be sent to the individual temperature sensor on a one-to-one basis in the detection process.

Figure 5:
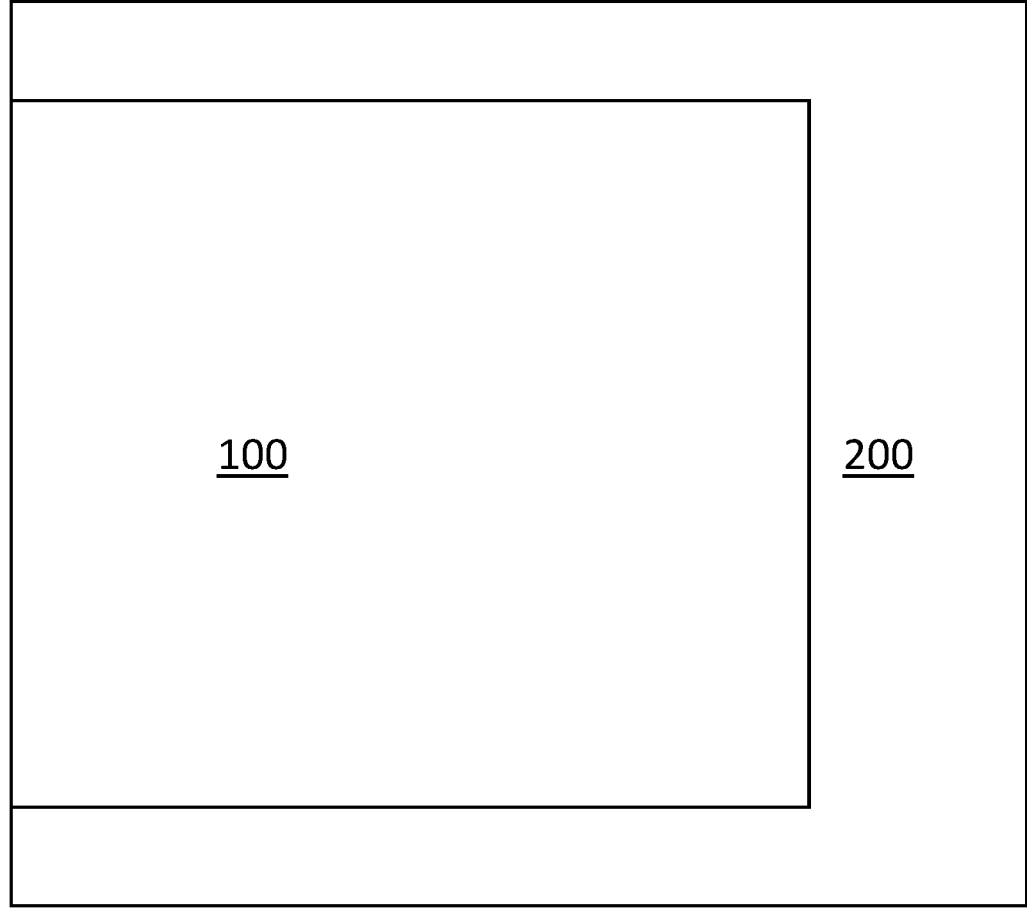
FIG. 5 is a schematic diagram showing an example circuit layout for hand temperature monitoring device according to an embodiment of the present invention.

Turning to FIG. 5, a simplified circuit layout of the sensing circuit system 200 is shown. The sensing array 100, which has 10,000 temperature sensors arranged in a square, are encircled by the components of the sensing circuit system 200 from three sides. The sensing array 100 is a 20 cm by 20 cm square that gives an area of 400 cm². The temperature sensor density in this arrangement is 25 sensors/cm². If a surface area of a fingertip is about 2 cm², there will be at least 50 temperature sensors in this given area. This can be translated to high-resolution and high-density thermal mapping for temperature measurement in a data-rich area. The data update frequency can reach 2 Hz. As previously discussed, heat distribution on a person's hand is an important diagnostic tool in Chinese medicine. The temperature difference between the finger tips and the palm, or even the center and outskirt of a palm will indicate different types of body conditions.

This two-side circuit layout has greater data capacity for larger surface area and overcomes electrical crosstalk caused by a densely packed circuit board which has all the components disposed on one-side of the board. A stable analog signal can be obtained at high speed and accuracy. After data processing a large number of resistance curves, the digital temperature numbers are obtained. The noise interference from the temperature sensors can be reduced. That overcomes the noise interference caused by the matrix temperature sensors. The electrically independent temperature sensors have individual calibration mechanism. This design allows high accuracy of temperature measurement to ±0.1° C. In addition, the carbon fiber boards can protect the components on two sides of the flexible circuit board.

Figure 6A:
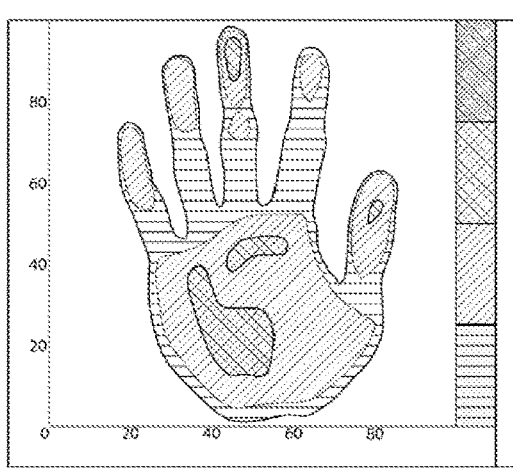
FIGS. 6A to 6C are diagrams showing hand temperature readouts from a hand temperature monitoring device according to an embodiment of the present invention.
Figure 6B:
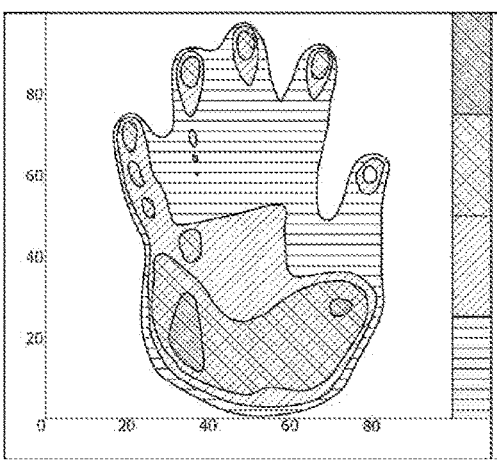
Figure 6C:
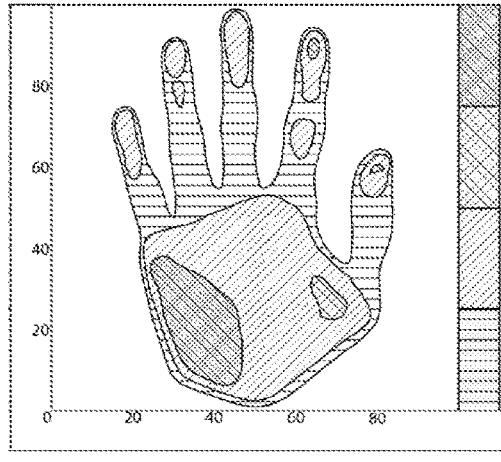

Turning to FIGS. 6A to 6C, hand temperature distribution diagrams obtained from the temperature monitoring device in accordance with an embodiment of the present invention are shown. The temperature data are collected on the temperature monitoring device and then transmitted and translated to the heat distribution diagrams on the computing device. The pattern bar on the right-hand side of each diagram represents temperature from low to high in four different ranges. When a person's hand makes contact with the carbon fiber board 150, as shown in FIG. 1, a difference of 0.1° C. of the hand temperature can be captured by the temperature monitoring device 102, as shown in FIG. 2. Three persons' hand temperatures are captured in FIGS. 6A to 6C respectively. Turning to FIG. 6A, the hand temperature distribution is even, and in general the hand temperature is at the lower range, apart from the center region of the palm. Turning to FIG. 6B, the hand temperature has a higher range at the palm and finger tips in comparison with other part of the hand. Turning to FIG. 6C, it shows a high temperature range at a particular portion of the person's palm. The temperature monitoring device 100/102 is accurate and able to tell apart the temperature difference between different areas of palm and between the palm and the fingers. With the addition of artificial intelligence analysis, the high-precision temperature distribution map can effectively monitor the minor temperature changes at real time.

The temperature monitoring device of the present invention can be used to monitor stroke recovery progress because a rise in hand temperature may indicate a potential stroke. This correlation can be found in the two different types of strokes, namely, ischemic and hemorrhagic stroke. Alternatively, the temperature monitoring device can be used in fertility diagnosis because progesterone causes a slight rise in female basal body temperature (BBT) during ovulation by approximately 0.17° C. This rise of BBT can be captured by the temperature monitoring device.

As used herein, terms "approximately", "basically", "substantially", and "about" are used for describing and explaining a small variation. When being used in combination with an event or circumstance, the term may refer to a case in which the event or circumstance occurs precisely, and a case in which the event or circumstance occurs approximately. As used herein with respect to a given value or range, the term "about" generally means in the range of ±10%, ±5%, ±1%, or ±0.5% of the given value or range. The range may be indicated herein as from one endpoint to another endpoint or between two endpoints. Unless otherwise specified, all the ranges disclosed in the present disclosure include endpoints. The term "substantially coplanar" may refer to two surfaces within a few micrometers (μm) positioned along the same plane, for example, within 10 μm, within 5 μm, within 1 μm, or within 0.5 μm located along the same plane. When reference is made to "substantially" the same numerical value or characteristic, the term may refer to a value within ±10%, ±5%, ±1%, or ±0.5% of the average of the values.

What is claimed is:

1. A hand temperature monitoring device comprising at least one sensing array, wherein the at least one sensing array comprises:

a flexible printed circuit board (110);

a plurality of temperature sensors (120) disposed on a first side (112) of the flexible printed circuit board (110);

a plurality of p-type metal-oxide semiconductor field-effect transistors (MOSFETs) (130) disposed on a second side (114) of the flexible printed circuit board (110) opposing to the temperature sensors (120), wherein each of the p-type MOSFETs (130) is electrically connected to one of the temperature sensors (120);

a polymer film (140) caping each of the temperature sensors (120) and the p-type MOSFETs (130) respectively; and a carbon fiber board (150) positioned over the polymer film (140);

wherein the carbon fiber board (150) comprises a solid resin film layer on one side and a dry fabric layer on the opposite side;

wherein the solid resin film layer is disposed for making a full and intimate contact with a mould surface and the dry fabric layer is disposed for contacting with the polymer film (140) for further curing;

wherein the dry fabric layer facilitates an air removal during a vacuum bag lamination process;

wherein the mould is made based on a subject's palm and since the solid resin film layer is disposed for making a full and intimate contact with a mould surface during manufacturing, a personalized hand temperature monitoring device for the subject is provided;

wherein the carbon fiber board (150) has a flexibility that matches with the flexible printed circuit board (110)'s flexibility so to function as a protector to the flexible printed circuit board (110) against external force, excessive bending, blocking sweat and grease permeation to electronic components disposed on the flexible printed circuit board (110); and where the carbon fiber board (150) has a thermal conductivity higher than copper so to function as a passive heat dissipation means to the flexible printed circuit board (110).

2. The hand temperature monitoring device of claim 1, wherein each of the temperature sensors (120) is electrically independent from each other and has a physically mirroring p-type MOSFETs (130) acting as an individual switch.

3. The hand temperature monitoring device of claim 1, wherein the at least one sensing array is flexible and bendable.

4. The hand temperature monitoring device of claim 1, further comprising:

a processor (260) having a control unit (262) and a data transmit unit (264);

a plurality of decoders (230) connected between the control unit (262) and rows of the temperature sensors (120);

a plurality of multiplexer (210) connected between the control unit (262) and columns of the temperature sensors (120); and a computing device connected to the data transmit unit (264).

5. The hand temperature monitoring device of claim 4, wherein a state of an individual temperature sensor (120) is configured to change based on a switching signal generated by the control unit (262).

6. The hand temperature monitoring device of claim 1, wherein each of the p-type MOSFET (130) comprises a gate electrode, a source electrode, and a drain electrode, the gate electrode is electrically connected to the flexible printed circuit board (110), the source electrode is electrically connected to a power source (220), and the drain electrode is electrically connected to the temperature sensor (120).

7. The hand temperature monitoring device of claim 1, wherein the temperature sensors (120) are negative temperature coefficient thermistors having two solder plated electrodes; and wherein the temperature sensors (120) are doped with P-doping or Boron in a dopant range between $5.00000e14$ cm$^{-3}$ and $6.00000e14$ cm$^{-3}$ for increased temperature sensitivity of the temperature sensors (120).

8. The hand temperature monitoring device of claim 1, wherein the temperature sensors (120) are carbon fiber reinforced cement-based composite resistors; and wherein the temperature sensors (120) are doped with P-doping or Boron in a dopant range between $5.00000e14$ cm$^{-3}$ and $6.00000e14$ cm$^{-3}$ for increased temperature sensitivity of the temperature sensors (120).

9. The hand temperature monitoring device of claim 1, further comprising a thermal cured epoxy (160) disposed between the flexible printed circuit board (110) and the temperature sensors (120) and between the flexible printed circuit board (110) and the p-type MOSFETs (130).

10. The temperature monitoring device of claim 1, wherein the temperature monitoring device causes no harm to a human subject.

11. The temperature monitoring device of claim 1, wherein the temperature monitoring device has a temperature measurement accuracy of approximately ±0.1° C.

12. The temperature monitoring device of claim 1, wherein the temperature monitoring device detects a temperature distribution across a plurality of regions of the subject's palm.

13. The temperature monitoring device of claim 1, wherein the temperature sensors (120) are arranged to have a center distance of 2 mm with an adjacent one so that a temperature change or difference between different parts of the subject's palm having at least a distance of 2 mm between them is detectable.

14. A temperature monitoring device for medical diagnosis and treatment comprising at least one sensing array, wherein the at least one sensing array comprises:

a flexible printed circuit board;

a plurality of temperature sensors disposed on a first side of the flexible printed circuit board;

a plurality of p-type metal-oxide semiconductor field-effect transistors (MOSFETs) disposed on a second side of the flexible printed circuit board opposing to the temperature sensors, wherein each of the p-type MOSFETs is electrically connected to one of the temperature sensors;

a polymer film caping each of the temperature sensors and the p-type MOSFETs respectively; and a carbon fiber board positioned over the polymer film;

wherein the carbon fiber board comprises a solid resin film layer on one side and a dry fabric layer on the opposite side;

wherein the solid resin film layer is disposed for making a full and intimate contact with a mould surface and the dry fabric layer is disposed for contacting with the polymer film for further curing;

wherein the dry fabric layer facilitates an air removal during a vacuum bag lamination process;

wherein the mould is made based on a subject's palm and since the solid resin film layer is disposed for making a full and intimate contact with a mould surface during manufacturing, a personalized hand temperature monitoring device for the subject is provided;

wherein the carbon fiber board has a flexibility that matches with the flexible printed circuit board's flexibility so to function as a protector to the flexible printed circuit board against external force, excessive bending, blocking sweat and grease permeation to electronic components disposed on the flexible printed circuit board; and where the carbon fiber board has a thermal conductivity higher than copper so to function as a passive heat dissipation means to the flexible printed circuit board.

15. The temperature monitoring device of claim 14, wherein each of the temperature sensors is electrically independent from each other and has a physically mirroring p-type MOSFETs acting as an individual switch.

16. The temperature monitoring device of claim 14, wherein the at least one sensing array is flexible and bendable.

17. The temperature monitoring device of claim 14, further comprising:

a processor having a control unit and a data transmit unit;

a plurality of decoder connected between the control unit and rows of the temperature sensors;

a plurality of multiplexer connected between the control unit and columns of the temperature sensors; and a computing device connected to the data transmit unit.

18. The temperature monitoring device of claim 17, wherein a state of an individual temperature sensor is configured to change based on a switching signal generated by the control unit.

19. The temperature monitoring device of claim 14, wherein each of the p-type MOSFET comprises a gate electrode, a source electrode, and a drain electrode, the gate electrode is electrically connected to the flexible printed circuit board, the source electrode is electrically connected to a power source, and the drain electrode is electrically connected to the temperature sensor.

20. The temperature monitoring device of claim 14, wherein the temperature sensors are negative temperature coefficient thermistors having two solder plated electrodes; and wherein the temperature sensors are doped with P-doping or Boron in a dopant range between $5.00000e14$ $cm^{-3}$ and $6.00000e14$ $cm^{-3}$ for increased temperature sensitivity of the temperature sensors.

21. The temperature monitoring device of claim 14, wherein the temperature sensors are carbon fiber reinforced cement-based composite resistors; and wherein the temperature sensors are doped with P-doping or Boron in a dopant range between $5.00000e14$ $cm^{-3}$ and $6.00000e14$ $cm^{-3}$ for increased temperature sensitivity of the temperature sensors.

22. The temperature monitoring device of claim 14, further comprising a thermal cured epoxy disposed between the flexible printed circuit board and the temperature sensors and between the flexible printed circuit board and the p-type MOSFETs.

23. The temperature monitoring device of claim 14, wherein the temperature monitoring device causes no harm to human subject.

24. The temperature monitoring device of claim 14, wherein the temperature monitoring device has a temperature measurement accuracy of approximately +0.1° C.

25. The temperature monitoring device of claim 14, wherein the temperature monitoring device is configured to detect a temperature distribution across a plurality of regions of the subject's palm.

26. The temperature monitoring device of claim 14, wherein the temperature sensors are arranged to have a center distance of 2 mm with an adjacent one so that a temperature change or difference between different parts of the subject's palm having at least a distance of 2 mm between them is detectable.

27. The temperature monitoring device of claim 14, further comprising a temperature record database for recording temperature distributions across a plurality of regions of a palm of each of one or more subjects so to serve for disease diagnosis and health management functions.

28. The temperature monitoring device of claim 14, wherein the temperature monitoring device monitors a stroke recovery progress, a fertility diagnosis, a coma recovery progress, a health condition of a patient admitted to intensive care unit (ICU) and an elder's health.

* * * * *